(12) United States Patent
Spears et al.

(10) Patent No.: US 12,629,403 B2
(45) Date of Patent: *May 19, 2026

(54) COMPOSITIONS AND METHODS FOR DIGESTIVE HEALTH IN AN FELINE

(71) Applicant: Société des Produits Nestlé S.A., Vevey (CH)

(72) Inventors: Julie Kristine Spears, St. Louis, MO (US); Alison Beloshapka, St. Louis, MO (US); Sandeep Bhatnagar, Ballwin, MO (US)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 245 days.

This patent is subject to a terminal disclaimer.

(21) Appl. No.: 18/452,676

(22) Filed: Aug. 21, 2023

(65) Prior Publication Data

US 2024/0100115 A1 Mar. 28, 2024

Related U.S. Application Data

(60) Provisional application No. 63/409,031, filed on Sep. 22, 2022.

(51) Int. Cl.
| | |
|---|---|
| *A61K 36/42* | (2006.01) |
| *A23K 10/30* | (2016.01) |
| *A23K 20/147* | (2016.01) |
| *A23K 20/163* | (2016.01) |
| *A23K 50/40* | (2016.01) |
| *A61K 31/733* | (2006.01) |
| *A61K 38/16* | (2006.01) |

(52) U.S. Cl.
CPC .............. *A61K 36/42* (2013.01); *A23K 10/30* (2016.05); *A23K 20/147* (2016.05); *A23K*

*20/163* (2016.05); *A23K 50/40* (2016.05); *A61K 31/733* (2013.01); *A61K 38/168* (2013.01)

(58) Field of Classification Search
None
See application file for complete search history.

(56) References Cited

U.S. PATENT DOCUMENTS

| | | | |
|---|---|---|---|
| 9,585,925 B1 | 3/2017 | Bascharon |
| 10,681,922 B2 | 6/2020 | Norton et al. |
| 2011/0212881 A1 | 9/2011 | Aimutis |

FOREIGN PATENT DOCUMENTS

| | | | |
|---|---|---|---|
| CN | 105943953 | * | 9/2016 |
| WO | 2017116449 | | 7/2017 |
| WO | 2020131007 A1 | | 6/2020 |
| WO | 2021133602 A1 | | 7/2021 |

OTHER PUBLICATIONS

Rosa-Sibakov et al., Trends in Food Science & Technology 41 (2015), pp. 118-134.*
Jupiter Science, 20 pages, 2025.*
Verywell Fit, 9 pages, 2025.*
International Search Report and Written Opinion to PCT/IB2023/058324 dated Nov. 5, 2023.

* cited by examiner

*Primary Examiner* — Michael V Meller

(57) ABSTRACT

Compositions and methods from providing a digestive health benefit to a feline include the use of a prebiotic fiber blend comprising pumpkin, inulin, and, optionally, wheat bran aleurone.

5 Claims, No Drawings

COMPOSITIONS AND METHODS FOR DIGESTIVE HEALTH IN AN FELINE

CROSS REFERENCE TO RELATED APPLICATION

This application claims priority to U.S. Provisional Application Ser. No. 63/409,031 filed Sep. 22, 2022 the disclosure of which is incorporated in its entirety herein by this reference.

BACKGROUND

The intestinal tract plays a critical role in animal health and wellness. To help fulfill this role, the intestinal tract contains various microorganisms that comprise a healthy gastrointestinal microflora under normal conditions. The microflora confers many benefits to the animal, e.g., the production of fatty acids that fuel the cells that line the gastrointestinal lumen, the synthesis of vitamins, and the synthesis of enzymes that aid in the breakdown and digestion of food. In addition, the microflora aids the immune system in host protection from disease. For example, microflora are known to inhibit the attachment to and colonization of potential pathogens within the gastrointestinal tract and to stimulate the production of cytokines and immunoglobulins.

Unfortunately, disruption of the normal balance of microflora can result in opportunistic infection of the gastrointestinal tract and can facilitate additional complications such as diarrhea and dehydration. The normal microflora balance can be disrupted through a variety of means, e.g., stress, advanced age, travel, consumption of contaminated food or water, antibiotic therapy, and the like. One method for preventing or treating such undesirable disruption involves prophylactically administering probiotics to an animal to prevent the disruption or to therapeutically administering probiotics to an animal to restore the normal microflora balance and facilitate recovery from the resulting undesirable complications caused by the disruption.

Probiotics and their benefits for animal health are well known to skilled artisans. Probiotics are live microorganisms that have a beneficial effect in the prevention and treatment of specific medical conditions when ingested. Probiotics are believed to exert biological effects through a phenomenon known as colonization resistance. Probiotics facilitate a process whereby the indigenous anaerobic flora limits the concentration of potentially harmful (mostly aerobic) bacteria in the digestive tract. Other modes of action, such as supplying enzymes or influencing enzyme activity in the gastrointestinal tract, may also account for some of the other functions that have been attributed to probiotics. Probiotics are known to enhance intestinal function, stimulate the immune system, reduce inflammation, and diminish the population of harmful microorganisms in the gastrointestinal tract.

While probiotics are generally useful for promoting the health of an animal, they are often difficult to store, handle, and administer to the animal. Probiotics may be unstable under normal environmental conditions and require special handling, e.g., refrigeration, freeze drying, or other means to prolong probiotic life. Similarly, probiotics are often unpalatable to the animal consuming them. Often, the palatability must be disguised or enhanced using other compounds or compositions. Further, it may be beneficial to supplement the immune system, particularly in the gastrointestinal tract, using ingredients in combination with the probiotics to obtain maximum benefit from probiotic administration.

Additionally, achieving therapeutic amounts can be challenging. There is, therefore, a need for new compositions that can provide digestive health benefits for animals.

SUMMARY

The present disclosure relates generally to compositions and methods for providing a digestive health benefit to a feline including the use of a prebiotic fiber blend.

In one embodiment, a prebiotic fiber blend for a feline can comprise pumpkin, inulin, and, optionally, wheat bran aleurone.

In another embodiment, a method of providing a digestive health benefit to a feline can comprise administering to the feline a prebiotic fiber blend, wherein the prebiotic fiber blend comprises pumpkin, inulin, and, optionally, wheat bran aleurone.

Other embodiments include treating diarrhea, increasing fecal quality, increasing microbiome diversity, reducing inflammation, increasing beneficial bacteria, reducing protein catabolites, reducing pathogenic bacteria, decreasing post-prandial glucose fluctuations, and combinations thereof, by administering the compositions are also described herein.

Additional features and advantages are described herein and will be apparent from the following Detailed Description.

DETAILED DESCRIPTION

Definitions

As used in this disclosure and the appended claims, the singular forms "a," "an" and "the" include plural referents unless the context clearly dictates otherwise. Thus, for example, reference to "a fiber" or "the fiber" includes two or more fibers. The term "and/or" used in the context of "X and/or Y" should be interpreted as "X," or "Y," or "X and Y." Where used herein, the terms "example" and "such as," particularly when followed by a listing of terms, are merely exemplary and illustrative, and are not exclusive or comprehensive.

As used herein, "about" is understood to refer to numbers in a range of numerals, for example the range of −10% to +10% of the referenced number, within −5% to +5% of the referenced number, or in one aspect, within −1% to +1% of the referenced number, and in a specific aspect, within −0.1% to +0.1% of the referenced number. Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

All percentages expressed herein are by weight of the total weight of the food composition unless expressed otherwise. When reference is made to the pH, values correspond to pH measured at 25° C. with standard equipment. An "amount" can be the total amount of the referenced component per serving of the composition or per distinct unit of the composition and/or can be the weight percentage of the referenced component by dry weight. Moreover, an "amount" includes zero; for example, the recitation of an amount of a compound does not necessarily mean that the compound is present, unless followed by a range that excludes zero.

The terms "pet food," "pet food product" and "pet food composition" mean a product or composition that is intended for ingestion by a feline that provides at least one nutrient to the feline. Further in this regard, these terms mean that the product or composition is in a form ready for consumption and is not merely an intermediate from which a consumable product or composition is made, although other food compositions can be added in some embodiments, such as a dietary supplement. The term "pet food" means any food composition intended to be consumed by a feline.

The term "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In one embodiment, the present fiber blend can be present in an effective amount for improving microbiome; improving or treating gastrointestinal issues; treating or preventing diarrhea; increasing or improving fecal quality; treating, preventing, or reducing inflammation; treating, preventing or decreasing post-prandial glucose fluctuations; and/or increasing or improving digestive health.

The dosages expressed herein are in milligrams per kilogram of body weight per day (mg/kg/day) unless expressed otherwise.

The term "long-term administration" means periods of repeated administration or consumption in excess of one month. Periods of longer than two, three, or four months can be used for certain embodiments. Also, more extended periods can be used that include longer than 5, 6, 7, 8, 9, or 10 months. Periods in excess of 11 months or 1 year can also be used. Longer term use extending over 1, 2, 3, or more years are included in the invention. For certain aging felines, the feline will continue consuming on a regular basis for the remainder of its life. This can also be referred to as consumption for "extended" periods.

The term "regular basis" or "regular administration" means at least monthly dosing with the compositions or consumption of the compositions, and in one aspect, means at least weekly dosing. More frequent dosing or consumption, such as twice or three times weekly, can be performed in certain embodiments. Still, in other embodiments, regimens can be used that comprise at least once daily consumption. A frequency, regardless of whether expressly exemplified herein, that allows maintenance of a desired activity level of the measured compound, such as a probiotic, within acceptable ranges can be useful herein. The skilled artisan will appreciate that feeding amounts will be a function of the composition that is being consumed or administered as well as the animal consuming the food, and some food compositions may require more or less frequent administration to maintain a desired activity level of the measured compound (e.g., a probiotic).

The relative terms "improve," "increase," "enhance," "decrease" and the like refer to the effects of the composition disclosed herein (a composition comprising a prebiotic fiber blend) relative to a composition having a lower amount or lacking such compositional elements, but otherwise identical.

A "blended" composition merely has at least two components having at least one different characteristic relative to each other. In one aspect, moisture content and water activity can be different in the context of the present disclosure. In this regard, description of a composition as "blended" does not imply that the blended composition has been subjected to processing sometimes referenced as "blending," namely mixing components so that they are indistinguishable from each other, and, in one aspect, such processing is avoided when mixing one component with the other components to form a blended composition (e.g., mixing a dry component with a wet or semi-moist component). Further in this regard, in a blended composition each of the at least two components having at least one different characteristic relative to each other can retain their distinct identity and appearance.

"Wet food" means a pet food having a moisture content from about 50% to about 90%, and in one aspect, from about 70% to about 90%. "Dry food" means a pet food having a moisture content less than about 20%, and in one aspect, less than about 15%, and in a specific aspect, less than about 10%. "Semi-moist food" means a pet food having a moisture content from about 20% to about 50%, and in one aspect, from about 25% to about 35%.

"Kibbles" is used synonymously with "chunks" herein and both terms mean pieces of dry or semi-moist pet food which can have a pellet shape or any other shape and can be made by slicing a food composition into separate pieces. Non-limiting examples of kibbles include particulates; pellets; pieces of pet food, dehydrated meat, meat analog, vegetables, and combinations thereof; and pet snacks, such as meat or vegetable jerky, rawhide, and biscuits. A "meat analog" is a meat emulsion product that resembles pieces of natural meat in appearance, texture, and physical structure.

The term "complete and balanced" when referring to a food composition means a food composition that contains all known required nutrients in appropriate amounts and proportions based on recommendations of recognized authorities in the field of animal nutrition, and are therefore capable of serving as a sole source of dietary intake to maintain life or promote production, without the addition of supplemental nutritional sources. Nutritionally balanced pet food and animal food compositions are widely known and widely used in the art, e.g., complete and balanced food compositions formulated according to standards established by the Association of American Feed Control Officials (AAFCO) as of Jan. 1, 2022.

The term "dietary supplement" or "supplement" refers to a product that is intended to be ingested in addition to a normal diet. Dietary supplements may be in any form, e.g., solid, liquid, gel, tablets, capsules, powder, and the like. In one aspect, they can be provided in convenient dosage forms. In some embodiments, they can be provided in bulk consumer packages such as bulk powders, liquids, gels, or oils. In other embodiments, supplements can be provided in bulk quantities to be included in other food items such as snacks, treats, supplement bars, beverages, and the like.

The compositions disclosed herein may lack any element that is not specifically disclosed herein. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified. Any embodiment disclosed herein can be combined with any other embodiment disclosed herein unless explicitly and directly stated otherwise.

The present discussion of embodiments, aspects, examples, etc. are independent in that they can apply to all methods and compositions. For example, a prebiotic fiber blend used in a food composition can also be used in the method of improving microbiome of an animal, and vice versa.

EMBODIMENTS

The present inventors have discovered that prebiotic fiber blends can provide digestive health benefits in a feline. Additionally, the present inventors have discovered that certain fiber blends unexpectedly provided specific health benefits for felines, which was not found in other companion animals.

As such, in one embodiment, a prebiotic fiber blend for a feline can comprise pumpkin, inulin, and, optionally, wheat bran aleurone. In one embodiment, the blend contains wheat bran aleurone.

In another embodiment, a method of providing a digestive health benefit to a feline can comprise administering to the feline a prebiotic fiber blend, wherein the prebiotic fiber blend comprises pumpkin, inulin, and, optionally, wheat bran aleurone. In one embodiment, the blend contains wheat bran aleurone.

Other embodiments include treating diarrhea, increasing fecal quality, increasing microbiome diversity, reducing inflammation, increasing beneficial bacteria, reducing protein catabolites, reducing pathogenic bacteria, decreasing post-prandial glucose fluctuations, and combinations thereof, by administering the compositions are also described herein.

Generally, the pumpkin, inulin, and wheat bran aleurone can be present in any effective amount that provides a therapeutic effect for a feline. In one embodiment, the pumpkin can be present in fiber blend in an amount from about 20% to about 50%. In one aspect, the pumpkin can be present in the fiber blend from about 20%, 25%, 30%, 35%, 40%, or 45%, to about 25%, 30%, 35%, 40%, 45%, or 50%. In one embodiment, the inulin can be present in the fiber blend in an amount from about 10% to about 40%. In one aspect, the inulin can be present in the fiber blend from about 10%, 15%, 20%, 25%, 30%, or 35%, to about 15%, 20%, 25%, 30%, 35%, or 40%. In one embodiment, the wheat bran aleurone can be present in the fiber blend in an amount from about 20% to about 50%. In one aspect, the wheat bran aleurone can be present in the fiber blend from about 20%, 25%, 30%, 35%, 40%, or 45%, to about 25%, 30%, 35%, 40%, 45%, or 50%.

Generally, the prebiotic fiber blend can be part of a food composition, e.g., a pet food composition, a treat, a supplement, etc. In one embodiment, a pet food composition can comprise the prebiotic fiber blends as described herein. In one aspect, the pet food composition can further comprise protein, carbohydrates and fat. In another aspect, the pet food composition can further comprise a preservative. Additionally, the other food compositions described herein can contain a preservative.

Generally, the prebiotic fiber blend can be present in the composition in any effective amount that confers a therapeutic effect or health benefit as described herein. In one embodiment, the fiber blend can be present in the pet food composition in an amount from about 0.1% to about 10%. In one aspect, the fiber blend can be present in the pet food composition in an amount from about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, 4.5%, or 5.0% to about 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10%. In another embodiment, the pet food composition can be a complete and balanced pet food. In one embodiment, the pumpkin can be present in pet food in an amount from about 0.01% to about 5%. In one aspect, the pumpkin can be present in the pet food from about 0.01%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, or 4.5%, to about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, 4.5%, or 5.0%. In one embodiment, the inulin can be present in the pet food in an amount from about 0.01% to about 5%. In one aspect, the inulin can be present in the pet food from about 0.01%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, or 4.5%, to about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, 4.5%, or 5.0%. In one embodiment, the wheat bran aleurone can be present in the pet food in an amount from about 0.01% to about 5%. In one aspect, the wheat bran aleurone can be present in the pet food from about 0.01%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, or 4.5%, to about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.5%, 3.0%, 3.5%, 4.0%, 4.5%, or 5.0%.

In other embodiments, the prebiotic fiber blend can be in the form of a supplement or a treat. In one embodiment, a supplement can comprise the prebiotic fiber blend. Additionally, in one aspect, the fiber blend can be present in the supplement in an amount from about 0.1% to about 50%. In various aspects, the fiber blend can be present in the supplement from about 5%, 10%, 15%, 20%, 25%, 30%, 35%, or 40%, to about 10%, 15%, 20%, 25%, 30%, 35%, 40%, 45%, or 50%. In another embodiment, a treat can comprise the prebiotic fiber blend. In one aspect, the fiber blend can be present in the treat in an amount from about 0.1% to about 50%. In various aspects, the fiber blend can be present in the treat from about 5%, 10%, 15%, 20%, 25%, 30%, 35%, or 40%, to about 10%, 15%, 20%, 25%, 30%, 35%, 40%, 45%, or 50%.

Generally, the present compositions are administered to a feline to provide a health benefit to the feline as described herein. In one embodiment, the prebiotic fiber blend can be administered to the feline on a regular basis. Such administration can be accomplished through any composition as described herein. In one embodiment, the prebiotic fiber blend can be administered to the feline as part of a pet food composition. In various aspects, the pet food composition can be a wet pet food, a dry pet food, a semi-moist pet food, or a blended pet food.

Generally, the present prebiotic fiber blends provide specific health benefits to a feline. In one embodiment, the digestive health benefit can be selected from the group consisting of treating diarrhea, increasing fecal quality, increasing microbiome diversity, reducing inflammation, increasing beneficial bacteria, reducing protein catabolites, reducing pathogenic bacteria, decreasing post-prandial glucose fluctuations, and combinations thereof.

Typically, the present compositions can be administered to the animal for a sufficient time to effect change in the animal's microbiome or to provide the health benefits as described herein. In one embodiment, the composition can be administered to the animal on a regular basis. In another embodiment, the composition can be administered long-term. As discussed herein, the present compositions are generally food compositions but can also be administered as part of a dietary regime in the form of supplements, treats, sachets, and the like. In one embodiment, the composition is a pet food composition. In another embodiment, the composition is a dietary supplement. In still another embodiment, the composition is a sachet.

Additionally, the compositions disclosed herein can contain other ingredients. In one embodiment, the compositions can contain probiotics or other prebiotics. Probiotics are live microorganisms that have a beneficial effect in the prevention and treatment of specific medical conditions when ingested. Probiotics are believed to exert biological effects through a phenomenon known as colonization resistance. The probiotics facilitate a process whereby the indigenous anaerobic flora limits the concentration of potentially harmful (mostly aerobic) bacteria in the digestive tract. Other modes of action, such as supplying enzymes or influencing enzyme activity in the gastrointestinal tract, may also account for some of the other functions that have been attributed to probiotics. Prebiotics are nondigestible food ingredients that beneficially affect host health by selectively stimulating the growth and/or activity of bacteria in the colon. Prebiotics include fructooligosaccharides (FOS), xylooligosaccharides (XOS), galactooligosaccharides (GOS), and mannooligosaccharides (typically for non-human foods such as pet foods). The prebiotic, fructooligosaccharide (FOS) is found naturally in many foods such as wheat, onions, bananas, honey, garlic, and leeks. FOS can also be isolated from chicory root or synthesized enzymatically from sucrose. FOS fermentation in the colon results in a large number of physiologic effects including increasing the numbers of bifidobacteria in the colon, increasing calcium absorption, increasing fecal weight, shortening of gastrointestinal transit time, and possibly lowering blood lipid levels. Probiotics enhance systemic cellular immune responses and may be useful as a dietary supplement to boost natural immunity in otherwise healthy adults. Probiotics include many types of bacteria but generally are selected from four genera of bacteria: *Lactobacilllus acidophillus, Bifidobacteria, Lactococcus,* and *Pediococcus.* Beneficial species include *Enterococcus* and *Saccharomyces* species. The amount of probiotics and prebiotics to be administered to the animal is determined by the skilled artisan based upon the type and nature of the prebiotic and probiotic and the type and nature of the animal, e.g., the age, weight, general health, sex, extent of microbial depletion, presence of harmful bacteria, and diet of the animal. Generally, probiotics are administered to the animal in amounts of from about one to about twenty billion colony forming units (CFUs) per day for the healthy maintenance of intestinal microflora, and in one aspect, from about 5 billion to about 10 billion live bacteria per day. Generally, prebiotics are administered in amounts sufficient to positively stimulate the healthy microflora in the gut and cause these "good" bacteria to reproduce. Typical amounts are from about one to about 10 grams per serving or from about 5% to about 40% of the recommended daily dietary fiber for an animal. The probiotics and prebiotics can be made part of the composition by any suitable means. Generally, the agents are mixed with the composition or applied to the surface of the composition, e.g., by sprinkling or spraying. When the agents are part of a kit, the agents can be admixed with other materials or in their own package. For embodiments of dietary supplements, such supplements can comprise from about 1% to about 90% probiotics, from about 1% to about 70% probiotics, or even, from about 1% to about 50% probiotics.

The compositions of the invention can comprise additional substances such as minerals, vitamins, salts, proteins, amino acids, fibers, antioxidants, condiments, colorants, and preservatives. Non-limiting examples of minerals include calcium, phosphorous, potassium, sodium, iron, chloride, boron, copper, zinc, magnesium, manganese, iodine, selenium and the like, and various salts thereof. Non-limiting examples of vitamins include vitamin A, various B vitamins (e.g., B-1, B-2, B-3, B-5, B-6, B-7, B-9, and B-12), vitamin D, and vitamin K. Non-limiting examples of antioxidants include butylated hydroxyanisole ("BHA") and butylated hydroxytoluene ("BHT"), vitamin E (tocopherols), and the like. Non-limiting examples of suitable preservatives include potassium sorbate, sorbic acid, sodium methyl para-hydroxybenzoate, calcium propionate, propionic acid, and combinations thereof. The compositions may also comprise carotenoids such as alpha-carotene, lycopene, lutein, zeaxanthin and beta-cryptoxanthin. Additional ingredients may also be included, for example, digestive aids, health aids, and the like.

In various embodiments, the compositions of the invention may further comprise from about 15% to about 60% crude protein. In one embodiment, the compositions comprise about 40% to about 55% crude protein. The crude protein material may comprise vegetable proteins such as soybean, corn, rice, cottonseed, and peanut, or animal proteins such as casein, albumin, and meat protein. Non-limiting examples of meat protein useful herein include pork, lamb, equine, poultry, fish, and mixtures thereof.

The compositions may further comprise from about 5% to about 40% fat. In one embodiment, the compositions can comprise about 15% to about 22% fat. The compositions may further comprise a source of carbohydrate. The compositions may comprise from about 15% to about 60% carbohydrate. Non-limiting examples of such carbohydrates include grains or cereals such as rice, corn, sorghum, alfalfa, barley, soybeans, canola, oats, wheat, and mixtures thereof. The compositions may also optionally comprise other materials such as dried whey and other dairy by-products.

The compositions may also further comprise other fiber sources. Generally, the compositions may comprise from about 0.5% to about 5% fiber. A variety of soluble or insoluble fibers may be utilized, as will be known to those of ordinary skill in the art. The fiber source can be beet pulp (from sugar beet), gum arabic, gum talha, *psyllium,* rice bran, carob bean gum, citrus pulp, pectin, fructooligosaccharide, mannanoligofructose, soy fiber, fiber from lupins, arabinogalactan, galactooligosaccharide, arabinoxylan, or mixtures thereof. The fiber source can be a fermentable fiber, as are many of those listed above. Fermentable fiber has previously been described to provide a benefit to the immune system of companion animals. Fermentable fiber or other compositions known to those of skill in the art which provide a prebiotic composition that could enhance the growth of probiotics within the intestine may also be incorporated into the composition to aid in the enhancement of the benefits provided by the present invention to the immune system gastrointestinal system, and general health of an animal.

In some embodiments where the composition is a supplement, to enhance the length of time the supplement can be stored, the dietary supplements can have a total moisture content between about 2% and about 10% by weight of the supplement. In one embodiment, the total moisture content can be less than 5% by weight of the supplement. Similarly, the dietary supplement can have a water activity in the range of 0.20 to 0.6. In one aspect, the water activity can be less than 0.55.

The compositions may be specially formulated for young, adult, or senior animals. In general, specialized formulations comprise ingredients that meet the energy and nutritional requirements appropriate for felines at different stages of development or age, or with specific nutrient requirements related to a disease state.

As discussed herein, the pet food composition can comprise meat, such as emulsified meat. Examples of suitable meat include poultry, beef, pork, lamb and fish, especially those types of meats suitable for pets. The meat can include any additional parts of an animal including offal. Some or all of the meat can be provided as one or more meat meals, namely meat that has been dried and ground to form substantially uniform-sized particles and as defined by AAFCO. Additionally or alternatively, vegetable protein can be used, such as pea protein, corn protein (e.g., ground corn or corn gluten), wheat protein (e.g., ground wheat or wheat gluten), soy protein (e.g., soybean meal, soy concentrate, or soy isolate), rice protein (e.g., ground rice or rice gluten) and the like.

In one embodiment, the pet food compositions disclosed herein can comprise vegetable oil, a flavorant, a colorant and water. Suitable vegetable oils include soybean oil, corn oil, cottonseed oil, sunflower oil, canola oil, peanut oil, safflower oil, and the like. Examples of suitable flavorants include yeast, tallow, rendered animal meals (e.g., poultry, beef, lamb, pork), flavor extracts or blends (e.g., grilled beef), animal digests, and the like. Suitable colorants include FD&C colors, such as blue no. 1, blue no. 2, green no. 3, red no. 3, red no. 40, yellow no. 5, yellow no. 6, and the like; natural colors, such as caramel coloring, annatto, chlorophyllin, cochineal, betanin, turmeric, saffron, paprika, lycopene, elderberry juice, pandan, butterfly pea and the like; titanium dioxide; and any suitable food colorant known to the skilled artisan.

In one embodiment, the pet food compositions can include a starch, such starches can include a grain such as corn, rice, wheat, barley, oats, soy and the like, and mixtures of these grains, and can be included at least partially in any flour. In another embodiment, the pet food compositions can include a humectant, such humectants include salt, sugars, propylene glycol and polyhydric glycols such as glycerin and sorbitol, and the like. In yet another embodiment, the pet food compositions can include an oral health care ingredient, such oral care ingredients include alfalfa nutrient concentrate containing chlorophyll, sodium bicarbonate, phosphates (e.g., tricalcium phosphate, acid pyrophosphates, tetrasodium pyrophosphate, metaphosphates, and orthophosphates), peppermint, cloves, parsley, ginger and the like.

Specific amounts for each additional ingredient in the pet food compositions disclosed herein will depend on a variety of factors such as the ingredient included in the first edible material and any second edible material; the breed of feline; the feline's age, body weight, general health, sex, and diet; the feline's consumption rate; the purpose for which the food product is administered to the feline; and the like.

EXAMPLES

The following non-limiting examples are illustrative of embodiments of the present disclosure.

Example 1—In Vitro Fiber Blend Study

An in vitro fermentation screening was performed on various fiber blends selected from 9 individual fibers, according to Table 1.

TABLE 1

| ID | Blend | Total Fiber (%) | Soluble (S) Fiber (%) | Insoluble (I) Fiber (%) | Ratio S:I |
|----|-------|-----------------|------------------------|--------------------------|-----------|
| 1 | Wheat bran aleurone, Barley, Beet pulp, Pumpkin | 39.7 | 9.2 | 30.5 | 23:77 |
| 2 | Barley, Oat fiber, Citrus fiber | 63.4 | 14.6 | 48.7 | 23:77 |
| 3 | Chicory inulin, Psyllium husk, Pumpkin | 33.8 | 22.8 | 10.8 | 68:32 |
| 4 | Chicory inulin, Oat fiber, Beet pulp, Pumpkin, Citrus fiber | 50.5 | 13.5 | 37.0 | 27:73 |
| 5 | Wheat bran aleurone, Chicory inulin, Pumpkin | 30.6 | 6.6 | 23.9 | 22:78 |
| 6 | Wheat bran aleurone, Cellulose, Beet pulp, Citrus fiber | 70.2 | 14.8 | 55.5 | 21:79 |

The blends were added in a concentration of 5 g/L to a sugar-depleted nutritional medium with a blank tube (no substrate) used for correction. Short-term colonic incubation simulation was performed using fresh fecal inoculum from a single healthy adult cat. Incubations were performed for 48 hours at 39° C. in anaerobic conditions with measurement at 24 hours. Each condition was measured in triplicate.

The results for 24-hour fermentation and 48-hour fermentation are shown in Tables 2 and 3, respectively. Overall microbial fermentation was measured using pH and gas production. Microbial metabolic activity was measured using saccharolytic end products: short chain fatty acids (SCFA) and lactate and proteolytic end products: branched short chain fatty acids (BCFA) and ammonium. Microbial community composition was measured via specific qPCR of Bacteroidetes, Firmicutes, *Bifidobacterium*, and *Lactobacillus* with Illumina® sequencing to provide relative abundance.

TABLE 2

| Parameter | Blend 1 | Blend 2 | Blend 3 | Blend 4 | Blend 5 | Blend 6 | Healthy Gut Shift |
|-----------|---------|---------|---------|---------|---------|---------|-------------------|
| pH | −0.09 | −0.08 | −0.20 | −0.15 | −0.19 | 0.00 | Decrease |
| Gas Production | 22.00 | 22.33 | 33.53 | 29.43 | 35.70 | 16.90 | Increase |
| Total SCFA | 20.80 | 12.78 | 24.76 | 19.24 | 21.48 | 9.55 | Increase |
| Acetate | 11.36 | 8.19 | 12.63 | 10.04 | 9.27 | 5.39 | Increase |
| Propionate | 5.16 | 2.22 | 9.46 | 6.07 | 7.84 | 1.71 | Increase |

TABLE 2-continued

| Parameter | Blend 1 | Blend 2 | Blend 3 | Blend 4 | Blend 5 | Blend 6 | Healthy Gut Shift |
|---|---|---|---|---|---|---|---|
| Butyrate | 2.91 | 1.73 | 2.31 | 2.26 | 3.20 | 1.64 | Increase |
| Lactate | −0.02 | −0.03 | −0.03 | −0.03 | 0.00 | 0.01 | Increase |
| Total BCFA | 0.12 | −0.15 | −0.44 | −0.26 | −0.39 | −0.21 | Decrease |
| Ammonium | −9.44 | −13.55 | −58.46 | −54.91 | −53.14 | −2.71 | Decrease |
| *Bacteroidetes* | 0.89 | 1.10 | 0.69 | 0.99 | 0.96 | 0.82 | Increase |
| *Firmicutes* | 0.69 | 0.83 | 1.00 | 1.04 | 0.92 | 0.86 | Increase |
| *Bifidobacterium* | 1.97 | 1.99 | 1.53 | 1.57 | 1.36 | 0.79 | Increase |
| *Lactobacillus* | 0.39 | 0.29 | 0.91 | 0.78 | 0.46 | 0.43 | Increase |
| *Akkermansia* | 0.45 | 0.50 | 0.61 | 0.53 | 0.36 | 0.60 | Increase |

TABLE 3

| Parameter | Blend 1 | Blend 2 | Blend 3 | Blend 4 | Blend 5 | Blend 6 | Healthy Gut Shift |
|---|---|---|---|---|---|---|---|
| pH | −0.16 | −0.15 | −0.25 | −0.19 | −0.21 | −0.05 | Decrease |
| Gas Production | 20.73 | 22.40 | 30.47 | 26.83 | 32.27 | 15.13 | Increase |
| Total SCFA | 18.53 | 14.61 | 26.47 | 17.90 | 20.29 | 12.36 | Increase |
| Acetate | 10.07 | 9.11 | 13.11 | 9.47 | 8.025 | 6.55 | Increase |
| Propionate | 5.26 | 3.15 | 10.45 | 6.11 | 8.06 | 2.76 | Increase |
| Butyrate | 2.98 | 2.33 | 2.98 | 2.48 | 3.77 | 1.80 | Increase |
| Lactate | 0.06 | 0.02 | 0.01 | 0.02 | 0.03 | 0.04 | Increase |
| Total BCFA | −0.07 | −0.09 | −0.26 | −0.36 | −0.28 | −0.05 | Decrease |
| Ammonium | −40.99 | −48.65 | −76.01 | −67.14 | −61.72 | −13.54 | Decrease |
| *Bacteroidetes* | 0.84 | 1.02 | 0.99 | 0.84 | 0.76 | 0.80 | Increase |
| *Firmicutes* | 0.43 | 0.60 | 0.69 | 0.52 | 0.47 | 0.35 | Increase |
| *Bifidobacterium* | 1.64 | 1.99 | 1.65 | 1.26 | 1.20 | 0.84 | Increase |
| *Lactobacillus* | 0.61 | 0.68 | 0.73 | 0.87 | 0.73 | 0.76 | Increase |
| *Akkermansia* | 0.06 | 0.04 | 0.17 | −0.02 | −0.07 | 0.14 | Increase |

As can be seen in Table 2, blends 3-5 provided generally positive results for the parameters measured with blend 3 and 5 performing the strongest. Notably, each of Blends 3-5 contain pumpkin and inulin. Blends 3-5 can be clearly distinguished as superior to blends 1-2 and 6, which provided unacceptable results. As such, blends 3-5 were pursued for in vivo testing.

Example 2—Feline Fiber Blend Study

An in vivo feline study was performed using 4 groups of 8 cats per group as outlined in Table X. All cats were apparently healthy, at least 1 year of age, and had not received antibiotics in the 60 days prior to the start of the test. In order to stabilize the intestinal microbiome, a control diet was fed to all cats for 28 days (Initial). At the end of the 28 days, cats were randomized to 1 of 4 treatment diets consisting of the control diet with added fiber blends. Cats were fed their allotted treatment diets for an additional 28 days (Final). All groups were balanced for age, weight, and sex. Measures were conducted on the same day of each Phase. A single fresh fecal sample was collected within 15 minutes of defecation and analyzed for fecal microflora via PCR, short chain and branched chain fatty acids. Data were analyzed to compare all results back to Initial for each cat. All groups were balanced for age, weight, and sex. Nutritional information for the pet foods incorporating the blends is provided in Table 5, percentages are based on the diet as fed. The pet foods were all found to be palatable.

TABLE 4

| Treatment Group | Age (year) | Weight (kg) | Ratio of Male:Female |
|---|---|---|---|
| Control* | 8.2 | 4.9 | 5:3 |
| Blend 3 | 8.5 | 5.3 | 4:4 |
| Blend 4 | 7.9 | 5.0 | 4:4 |
| Blend 5 | 8.5 | 5.3 | 5:3 |

*Purina Pro Plan ® Veterinary Diets EN Gastroenteric Feline Formula

TABLE 5

| Assay | Control* | Blend 3 | Blend 4 | Blend 5 |
|---|---|---|---|---|
| Moisture, % | 7.0 | 7.0 | 10.5 | 8.7 |
| Protein, % | 51.9 | 48.7 | 45.7 | 49.1 |
| Fat, % | 16.5 | 16.6 | 16.7 | 16.2 |
| Crude Fiber, % | 1.0 | 1.3 | 2.1 | 1.3 |
| Total Dietary Fiber (TDF), % | 6.2 | 9.1 | 9.0 | 7.6 |
| Insoluble Dietary Fiber (IDF), % | 5.7 | 7.8 | 7.7 | 6.8 |
| Soluble Dietary Fiber (SDF), % | 0.5 | 1.3 | 1.3 | 0.8 |
| SDF:IDF | 0.09 | 0.17 | 0.17 | 0.12 |
| SDF:TDF | 0.08 | 0.15 | 0.15 | 0.11 |
| Beet pulp, % | 0 | 0 | 3.5 | 0 |
| Pumpkin, % | 0 | 1.5 | 1.5 | 1.5 |
| Oat Fiber, % | 0 | 0 | 0.8 | 0 |
| Citrus Fiber, % | 0 | 0 | 0.2 | 0 |
| Psyllium, % | 0 | 1.5 | 0 | 0 |
| Inulin, % | 0 | 1.0 | 1.0 | 1.0 |
| Wheat Bran Aleurone, % | 0 | 0 | 0 | 1.5 |

*Purina Pro Plan ® Veterinary Diets EN Gastroenteric Feline Formula

While each blend provided generally acceptable digestibility and fecal quality, blend 5 was superior in increased beneficial bacteria, reduction of pathogenic bacteria, and reduction of protein catabolites as show in Table 6.

TABLE 6

| Parameter | Control | | Blend 3 | | Blend 4 | | Blend 5 | |
|---|---|---|---|---|---|---|---|---|
| | Initial | Final | Initial | Final | Initial | Final | Initial | Final |
| *Bifidobacteria* (log gc/g) | 6.4 | 6.5 | 6.7 | 6.9 | 6.8 | 7.0 | 6.6 | 7.2 |
| *Streptococcus* (log DNA/g) | 5.7 | 5.9 | 5.2 | 5.2 | 4.7 | 3.5 | 4.4 | 3.6 |
| Dysbiosis Index | −2.5 | −2.0 | −3.6 | −2.9 | −4.0 | −5.0 | −4.1 | −5.2 |
| Isovaleric acid (ng/mg) | 11.5 | 8.9 | 7.7 | 9.0 | 15.0 | 15.3 | 10.5 | 8.3 |
| Total BCFA (ng/mg) | 19.2 | 16.5 | 13.5 | 15.0 | 24.1 | 23.5 | 19.2 | 15.4 |
| IL-12 (pg/ml) | 472.9 | 414.1 | 440.2 | 400.6 | 433.8 | 391.6 | 479.4 | 428.7 |
| RANTES* (pg/ml) | 73.1 | 56.9 | 80.6 | 65.4 | 83.2 | 79.7 | 97.3 | 91.3 |

*Regulated upon Activation, Normal T Cell Expressed and Presumably Secreted

Example 3—Canine Fiber Blend Study

A canine study was also performed testing the same fiber blends. However, while fiber blends 3-5 provided acceptable in vitro screening, in vivo testing showed that blend 3 was superior to blend 5 in dogs in providing reduction of pathogenic bacteria, increased mobility, increased fecal IgA, and reduction of protein catabolites. As such, the results showed that the fiber blends do not perform the same across species.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A capsule, emulsion, tablet, kibble, pellet or supplement bar consisting essentially of pumpkin, chicory inulin, wheat bran aleurone and a probiotic, wherein the kibble is a ground meal shaped into a solid form.

2. The capsule, emulsion, tablet, kibble, pellet or supplement bar of claim 1, further consisting essentially of protein, carbohydrates, fat, and a preservative, wherein the pumpkin, chicory inulin, and wheat bran aleurone are present in an amount from about 0.1% to about 10%.

3. The capsule, emulsion, tablet, kibble, pellet or supplement bar of claim 1, wherein the pumpkin is present in an amount from about 0.01% to about 5%, the chicory inulin is present in an amount from about 0.01% to about 5%, and the wheat bran aleurone is present in an amount from about 0.01% to about 5%.

4. The capsule, emulsion, tablet, kibble, pellet or supplement bar of claim 1, wherein the capsule, emulsion, tablet, kibble, pellet or supplement bar is a complete and balanced pet food.

5. The capsule, emulsion, tablet, kibble, pellet or supplement bar of claim 1, wherein the capsule, emulsion, tablet, kibble, pellet or supplement bar consists essentially of pumpkin, chicory inulin, and wheat bran aleurone in an amount from about 0.1% to about 50%.

\* \* \* \* \*